United States Patent [19]
Nakagami et al.

[11] Patent Number: 5,858,411
[45] Date of Patent: Jan. 12, 1999

[54] SUSTAINED-RELEASE GRANULAR PREPARATIONS AND PRODUCTION PROCESS THEREOF

[75] Inventors: Hiroaki Nakagami; Masazumi Kojima; Shinji Sagasaki, all of Tokyo, Japan

[73] Assignee: Daiichi Pharmaceutical Co., Ltd., Tokyo, Japan

[21] Appl. No.: 849,457

[22] PCT Filed: Dec. 18, 1995

[86] PCT No.: PCT/JP95/02594

§ 371 Date: Jun. 19, 1997

§ 102(e) Date: Jun. 19, 1997

[87] PCT Pub. No.: WO96/19200

PCT Pub. Date: Jun. 27, 1996

[30] Foreign Application Priority Data

Dec. 19, 1994 [JP] Japan .................................. 6-314414

[51] Int. Cl.$^6$ .................................................... A61K 9/16
[52] U.S. Cl. .......................... 424/489; 424/470; 514/951
[58] Field of Search ................................... 424/489, 452, 424/457, 458, 468, 469, 470

[56] References Cited

U.S. PATENT DOCUMENTS

| | | | |
|---|---|---|---|
| 4,329,451 | 5/1982 | Zweigle | 536/77 |
| 4,330,338 | 5/1982 | Banker | 106/197 |
| 5,326,572 | 7/1994 | Mehra et al. | 424/484 |

*Primary Examiner*—Thurman K. Page
*Assistant Examiner*—James M. Spear
*Attorney, Agent, or Firm*—Oblon, Spivak, McClelland, Maier & Neustadt, P.C.

[57] ABSTRACT

This invention relates to sustained-release granular preparations obtained by wet-granulating an aqueous suspension, which comprises a medicinal ingredient, a fine particulate polymer having an average particle size not greater than 50 $\mu$m and a plasticizer, into granules and treating said granules at a temperature not less than the lower one of a minimum filmforming temperature and glass transition temperature of a mixture of said polymer and said plasticizer. This invention is also concerned with a process for the production of the sustained-release granular preparations. According to the present invention, granular preparations having an excellent sustained-release property and a high safety to the human body can be easily produced in a simple manner.

8 Claims, No Drawings

SUSTAINED-RELEASE GRANULAR PREPARATIONS AND PRODUCTION PROCESS THEREOF

This application is a 371 of PCT/JP95/02594 filed Dec. 18, 1995.

TECHNICAL FIELD

This invention relates to sustained-release granular preparations permitting control of the release rates of their medicinal ingredients and also to a production process thereof.

BACKGROUND ART

Sustained release preparations have a function to control the release rate of its medicinal ingredient, and they can maintain the effective blood level of the medicinal ingredient for a long time following administration to patients. In addition, it can also reduce the frequency of administration so that the compliance and QOL (quality of life) of the patient can be improved. Further, control of a blood level of the medicinal ingredient in the range of its minimum effective level to its minimum toxic level can make assure its effectiveness and safety to the human body.

Such sustained release preparations include preparations wherein a medicinal ingredient is coated with a film and preparations of matrix type wherein a medicinal ingredient is dispersed in a matrix. Illustrative preparation forms include multiple-unit preparations and single unit preparations. These multiple-unit preparations in turn include granules and fine granules, which are composed of a number of subunits, and capsules and tablets containing granules or pellets which promptly disintegrate into subunits in the digestive tract after oral administration thereof. On the other hand, such single unit preparations include non-disintegrative matrix tablets, and tablets coated with a release-controlling film.

Multiple-unit preparations are advantageous over single unit preparations in that they have high reproducibility of movement in the digestive tract, have a lower hazardous problem of local irritation owing to their movement in a wide-spread manner through the digestive tract, and permit administration in portions [Isao Sugimoto et al., "(Seizai Kaihatsu No Jissai To Kadai (Practice and Problems in the Development of Dosable Preparations)", Chapter 3, 215–228, 1986, R & D Planning]. As a production method of multiple-unit preparations, commonly employed is a method in which granules with a medicinal ingredient contained therein are coated with a release-controlling film is commonly employed. Also proposed include a method in which ion-exchange resin beads with a medicinal ingredient bound thereon are coated with a polymer, a method in which granules with a medicinal ingredient dispersed in an enteric solid are prepared by solid dispersion, a method in which matrix-type granules or fine granules with a medicinal ingredient dispersed in a polyglycerin fatty acid ester are formed by spray chilling [Japanese Patent Laid-Open No. 223533/1990], and as a production method of sustained-release granular preparations of a dihydropyridine-type Ca channel blocker, a method in which the sustained-release granular preparations are produced by extrusion granulation while using an enteric polymer, especially a water-base latex dispersion of a methacrylic acid copolymer LD as a binder (European Patent Application No. 87118948.6 filed on Dec. 21, 1987).

However, the coating method causes a safety problem to the human body because a polymer is dissolved using an organic solvent. Further, there is another problem that cumbersome control is required because the dissolution rate of a medicinal ingredient varies by a change in the thickness of a coating film or in the size of pores present in the coating film. Moreover, the coating method is accompanied by a further problem that, if a crack is formed in the coating film, the medicinal ingredient is rapidly released. On the other hand, in the method in which matrix-type granules or fine granules are produced, production procedures and quality control are relatively easy. It is, however, accompanied by a problem that a special apparatus such as a spray-chilling drier has to be used to obtain granular preparations.

Incidentally, Japanese Language Laid-Open Publication (PCT) No. 503315/1990 discloses a process for producing sustained-release dosable preparations by blending a medicinal ingredient and a polymer having a glass transition temperature (Tg) of from 30° to 150° C. into a raw material composition and forming the raw material composition into a predetermined shape, in which the raw material composition is maintained at the glass transition temperature or at a temperature higher than the glass transition temperature for a time sufficient to impart a preparation form having sustained-release property. This process, however, requires addition of the polymer after its dissolution in an organic solvent or addition of the polymer as a latex dispersion by dissolving it in an organic solvent and then emulsifying the resulting solution in water. Regarding preparation forms, its Examples also disclose only tablets. Application of this process for the production of granular preparations failed to provide the resulting preparations with fully satisfactory sustained-release property.

Accordingly, it has been desired to develop a process which makes it possible to easily produce a sustained-release granular preparations of the matrix type without using any special apparatus.

DISCLOSURE OF THE INVENTION

Under such circumstances as described above, the present inventors have proceeded with an extensive investigation. As a result, it has been found that a granular preparation having excellent sustained-release property can be easily produced by wet-granulating method, which comprises wet-granulating an aqueous suspension, which comprises a medicinal ingredient, a fine particulate polymer having an average particle size not greater than 50 μm and a plasticizer, into granules and treating said granules at at a temperature not less than the lower one of a minimum film-forming temperature and glass transition temperature of a mixture of said polymer and said plasticizer, leading to the completion of the present invention.

Namely, the present invention provides a process for the production of sustained-release granular preparations, which comprises wet-granulating an aqueous suspension, which comprises a medicinal ingredient, a fine particulate polymer having an average particle size not greater than 50 μm and a plasticizer, into granules and treating said granules at a temperature not less than the lower one of a minimum film-forming temperature and a glass transition temperature of a mixture of said polymer and said plasticizer, and also the resulting sustained-release granular preparations produced by the above process.

BEST MODE FOR CARRYING OUT THE INVENTION

No particular limitation is imposed on the medicinal ingredient available in the sustained-release granular preparations according to the present invention. As long as medicinal ingredients are orally dosable and are solid at room temperature like tranexamic acid, cetraxate hydrochloride, ticlopidine hydrochloride, ofloxacin, levofloxacin, cephem antibiotics, theophylline and procainamide hydrochloride, they are all available. Such medicinal ingredients are usually employed in the form of powders, and their particle sizes are preferably 250 $\mu$m or smaller in general.

The term "polymer" as used herein does not mean an emulsion-like latex polymer or pseudolatex polymer but means a solid, specifically powdery high-molecular compound obtained by conducting a polymerization reaction, a polymerizing reaction or the like in a usual manner or a powdery high-molecular compound produced by drying a latex polymer or a pseudolatex polymer. Illustrative examples include ethylcellulose, cellulose acetate, cellulose acetate phthalate, carboxymethylcellulose, methacrylic acid-methyl methacrylate copolymers methacrylic acid copolymer L, methacrylic acid copolymer S, etc.), ethyl acrylate-methyl methacrylatetrimethyl ammonioethylmethacrylate chloride copolymers (aminoalkyl methacrylate copolymers RS), hydroxypropyl methylcellulose phthalates (hydroxypropyl methylcellulose phthalate 200731, hydroxypropyl methylcellulose phthalate 200824, etc.), hydroxypropyl methylcellulose acetate succinate, ethylene-vinyl acetate copolymer, polyvinyl acetate, shellac, and the like. These polymers can be used either singly or in combination. In the present invention, it is preferred from the viewpoint of temperature control to employ a polymer which, when mixed with the plasticizer to be described subsequently herein, gives a minimum film-forming temperature or a glass transition temperature of about 100° C. or lower, desirably 90° C. or lower. From this standpoint, it is preferred to employ as the polymer ethylcellulose, methacrylic acid-methyl methacrylate copolymer, ethyl acrylate-methyl methacrylate-trimethylammonioethyl methacrylate chloride copolymer, hydroxypropyl methylcellulose phthalate, hydroxypropyl methylcellulose acetate succinate, carboxymethyl ethylcellulose, cellulose acetate phthalate or the like.

The term "minimum film-forming temperature (hereinafter abbreviated as "MFT") means a minimum drying temperature at which latex particles undergo deformation and fusion into a continuous film under a capillary attraction produced in inter-particle capillaries. MFT is determined by properties of a polymer, colloidal property of a latex, environmental conditions, etc. of these, the MFT is dependent especially on the glass transition temperature (Tg) of the polymer and indicates a temperature around the Tg [see Soichi Murai, "Latex No Kagaku (Chemistry of Latex)", Kobunshi Kankokai, Tokyo Japan]. It is not only a latex polymer or a pseudolatex polymer but also a mixture of a fine particulate polymer and a plasticizer, said mixture being useful in the practice of the present invention, that has an MFT. Whichever the case may be, the MFT varies depending on the amount of the plasticizer to be added. In general, MFT goes down by increasing the amount of an added plasticizer. Measurement of such an MFT can be performed by a method known per se in the art, for example, in accordance with the temperature gradient plate method devised by Protzman et al. in J. Appl. Polymer Sci., 4, 81, 1960 or the method described in the periodical, Chem. Pharm. Bull., 42(3), 656–662, 1994.

Further, "glass transition temperature" (hereinafter abbreviated as "Tg") is one of important parameters for specifying physical properties of a polymer. When a polymer in a liquid form is cooled under certain conditions, the polymer is frozen into a glassy state via a supercooled liquid. A phenomenon in which, as mentioned immediately above, a polymer changes into a glassy state without crystallization is called "glass transition". The temperature at that polymer's transition phenomenon is called "Tg". In essence, this transition phenomenon is a freezing phenomenon and is a sort of relaxing phenomenon. Described specifically, the liquid state cannot follow the cooling temperature, resulting in a glassy state which can be considered as having frozen during an observation period (segment motion → micro-Brownian motion → freezing). Accordingly, a temperature lower than or equal to Tg causes no micro-Brown motion of molecules, leading to substantial changes in physical properties, especially to significant changes in the coefficient of expansion, transmission, heat capacity, refractive index and hardness [see "IIyakuhin No Kaihatsu (Development of Pharmaceuticals), Vol. 12: Seizai Sozai (Pharmaceutical Necessities)", Hirokawa Publishing Co., Tokyo, Japan; "Kobunshi Kagaku No Kiso (Fundamental of High Molecular Chemistry)", Tokyo Kagaku Dojin, Tokyo, Japan]. Such Tg also varies by the addition of a plasticizer. similarly to MFT, Tg generally tends to go down by increasing the amount of an added plasticizer.

The average particle size of the polymer is 50 $\mu$m or smaller in general. An average particle size not greater than 20 $\mu$m but not smaller than 1 $\mu$m is particularly preferred from the standpoint of obtaining marked sustained-release property. An average polymer particle size greater than 50 $\mu$m makes it difficult to obtain a granular preparation having preferred sustained-release property. The term "average particle size" as used herein means a volume mean particle size measured by a laser diffraction particle size distribution measuring instrument.

No particular limitation is imposed on a method which is available for finely grinding the polymer. Applicable methods include, for example, a method using a grinding machine such as a jet mill or ball mill and to spray-drying a dispersion of a latex of the polymer.

Although no particular limitation is imposed on the amount of the polymer to be added, the polymer can be added generally in an amount 0.001 to 10,000 times by weight as much as the medicinal ingredient. However, from the standpoint of obtaining better sustained-release property as an advantageous effect, it is preferred to add the polymer in an amount 0.001 to 50 times by weight as much as the medicinal ingredient.

Illustrative examples of the plasticizer employed in the present invention include alkyl citrates such as triethyl citrate, acetyl triethyl citrate, tributyl citrate and acetyl tributyl citrate; sucrose fatty acid esters; glycerin mono-, di- and tri-fatty acid esters such as triacetin, glycerin mono-fatty acid esters, glycerin monostearate and acetylated monoglyceride; polyglycerin fatty acid esters; polyethylene glycols such as macrogol 400, macrogol 600, macrogol 1500, macrogol 4000 and macrogol 6000; tributyl sebacate; propylene glycol; sesame oil; castor oil; glycerin; silicone resins; D-sorbitol; phytosterol; alkyl phthalates such as diethyl phthalate, dibutyl phthalate and dioctyl phthalate; adipate polyesters; isopropyl myristate; medium chain triglyceride; butyl phthalyl butyl glycolate; and polyoxyethylene polyoxypropylene glycol. They can be used either singly or in combination. Of these, preferred for use in the present invention from the stand point of general-purpose applicability and simplicity are alkyl citrates such as triethyl citrate, acetyl triethyl citrate, tributyl citrate and acetyl tributyl citrate; glycerin mono-, di- and tri-fatty acid esters such as triacetin; polyethylene glycols such as macrogol 400, macrogol 1500 and macrogol 6000; alkyl phthalates such as diethyl phthalate and dibutyl phthalate; and propylene glycol.

The plasticizer can be added in such an amount that the resulting mixture of the plasticizer and the above-described polymer has an MFT or Tg of preferably not more than about 100° C., more preferably not more than 90° C. It is therefore preferred to add the plasticizer in an amount 0.001 to 5 times, notably 0.01 to 1 times by weight parts as much as the polymer.

The granular preparations according to the present invention can also contain, as needed, one or more of additives generally employed for the production of granular preparations and fine granular preparations, for example, excipients such as lactose, starch and crystalline cellulose; binders such as hydroxypropyl cellulose, polyvinyl pyrrolidone and hydroxypropyl methylcellulose; disintegrators such as calcium carboxymethylcellulose, low-substituted hydroxypropylcellulose and croscarmellose sodium; surfactants such as polysorbate 80, sodium laurylsulfate and "Pluronic" (trade mark); lubricant such as magnesium stearate; glidants; wetting agents; coloring matters; and bioadhesive polymers such as carboxyvinyl polymer, sodium alginate and sodium carboxymethylcellulose. The excipient can be added in a usual amount and regarding its particle size, it is generally sufficient to set it at 600 $\mu$m or smaller in the case of lactose, at 100 $\mu$m or smaller in the case of starch, and at 250 $\mu$m or smaller in the case of crystalline cellulose. Further, the amount of the binder to be added can usually be 1 to 5 wt. % based on the total weight of the granular preparations according to the present invention. As to the particle size of the binder, it is generally sufficient to set it at 500 $\mu$m or smaller in the case of hydroxypropyl cellulose, at 250 $\mu$m or smaller in the case of polyvinyl pyrrolidone, and 180 $\mu$m or smaller in the case of hydroxypropyl methylcellulose. The amount of the disintegrator to be added can usually be 1 to 20 wt. % based on the total weight of the granular preparations according to the present invention. With respect to the particle size of the disintegrator, it is generally sufficient to set it at 75 $\mu$m or smaller in the case of calcium carboxymethylcellulose, at 180 $\mu$m or smaller in the case of low-substituted hydroxypropyl cellulose, and at 75 $\mu$m or smaller in the case of croscarmellose sodium. Further, regarding the amounts and particle sizes of the glidant, wetting agent, coloring matter, surfactant and lubricant, those having commercially-available particle sizes can be used in usual amount ranges, specifically in amounts of 1% based on the total weight of the granular preparations according to the present invention. With respect to particle size of the bioadhesive polymers, commercially available polymer's particle size can be selected in view of availability, and those polymers can be used in an amount of usually from 1 to 20% based on the total weight of the granular preparations according to the present invention.

The granular preparations according to the present invention can be obtained by wet-granulating an aqueous suspension of the above-described ingredients. Upon wet granulation, it is preferred to homogeneously suspend the plasticizer in water in advance. Water is generally sufficient when used in an amount of 0.1 to 1 times by weight parts as much as the total weight of solid ingredients employed. In the present invention, an aqueous suspension consisting of ingredients and a binder solution or water is granulated by a wet-granulation method. Usable examples of the wet-granulation method include (1) the extrusion granulation method in which water or the like is added to powdery raw materials, the resulting mixture is kneaded, and the mass so kneaded is pressed against a die or a screen for its extrusion therethrough, whereby the kneaded mass is formed, that is, granulated; (2) the mixing and agitating granulation method in which powdery raw materials are mixed with a binder solution or water and under mixing and agitation, the resulting mixture is granulated; (3) the high-speed mixing and agitating granulation method, which is to conduct the mixing and agitating granulation method under a high shear force, namely, in which powdery raw materials are added with a binder solution or water and are granulated while mixing, agitating and fluidizing the powdery raw materials at a high speed; (4) the fluidized bed granulation method in which a fluidized bed of powdery raw materials is formed by an air stream and a binder solution of water is sprayed into the fluidized bed under drying conditions so that particles are caused to cohere into grains by liquid linkage; and (5) the rolling granulation method in which rolling raw materials is sprayed or coated with a binder or water to form spherical particles [see "Iyakuhin No Kaihatsu (Development of Pharmaceuticals)", Volume 11: "Seizai No Tan-i Sousa To Kikai (Unit Operations and Machines for the Production of Dosable Preparations)", Hirokawa Publishing Co., Tokyo, Japan]. These methods are all usable in the present invention.

The target sustained-release granular preparations can be obtained by treating the granules, which have been obtained by the above-described wet granulation, at a temperature not less than the lower one of the MFT and Tg of the mixture of the polymer and the plasticizer, specifically by allowing the granules to stand where the treatment temperature is in the range of room temperature or by heating the granules where the treatment temperature is higher than room temperature. In general, however, treatment at a temperature equal to or higher than the Tg of the polymer can provide granular preparations having sufficient sustained-release effect. In general, the treatment temperature can be set preferably at a temperature higher from 10 to 50° C. than the lower one of the MFT and Tg of the used polymer. A treatment time of 1 to 24 hours is sufficient.

Although no particular limitation is imposed on the particle size of the sustained-release granular preparations, the particle size can generally range from 10 μm to 170 μm. In the case of fine granules, however, it is preferred to control the content of granules smaller than 75 μm at 10 wt. % or less, the content of granules equal to and greater than 75 μm but smaller than 500 μm at 85 wt. % or more, and the content of granules equal to and greater than 500 μm but smaller than 850 μm at 5 wt. % or less. In the case of a granular preparation, on the other hand, it is preferred to control the content of granules smaller than 355 μm at 15 wt. % or less, the content of granules equal to and greater than 355 μm but smaller than 1,400 μm at 80 wt. % or more, and the content of granules equal to and greater than 1,400 μm but smaller than 1,700 μm at 5 wt. % or less.

The granular preparations according to the present invention can be formed into capsules by filling it in capsules in a manner known per se in the art. It can also be compressed into tablets together with an excipient, a disintegrator and a lubricant, as needed.

The present invention will hereinafter be described in further detail by the following Examples. It is however be borne in mind that the present invention is not limited to the following Examples.

EXAMPLE 1 AND COMPARATIVE EXAMPLE 1

In accordance with the formulas shown in Table 1, granular preparations were produced as will be described below. By conducting the following dissolution test, an investigation was carried out about any difference in sustained release property depending on whether the plasticizer was contained or not.

(Dissolution test)

The dissolution test was conducted following Method 2 (the paddle method) described under General Tests, Processes and Apparatus in The Pharmacopoeia of Japan, Twelfth Edition (JPXII). Described specifically, the preparation in an amount equivalent to 100 mg in terms of theophylline was immersed in 900 ml of water, followed by rotation of a stirring wing at 100 rpm to cause dissolution of the medicinal ingredient from the preparation. The dissolved solution was periodically sampled and filtered. The absorption of each filtrate so obtained was measured, and a dissolution rate was calculated from the absorption.

TABLE 1

| Formula (g) | Example 1 | Comp. Ex. 1 |
| --- | --- | --- |
| Theophylline (THEO) | 15 | 15 |
| Ethyl cellulose (EC)*[1] | 110 | 110 |
| Triethyl citrate (TEC) | 25 | — |
| Polysolbate 80 (Tween 80) | Trace | Trace |
| Total | 150 | 125 |
| Tg (°C.) | 36*[2] | ≈130*[3] |
| MFT (°C.) | 65*[2] | — |

*[1] Fine particle grade (volume mean particle size: 10.0 μm); N-10-F, Shin-Etsu Chemical Co., Ltd.
*[2] Estimated from the data shown in Chem. Pharm. Bull., 42(3), 656–662 (1994)
*[3] Int. J. Pharm. 27, 267–277(1985)
Int. J. Pharm. 34, 93–103(1986)
J. Pharm. Pharmacol., 31, 269–277(1979)

First, polysorbate 80 was dissolved in 75 ml of water, in which triethyl citrate was homogeneously suspended to obtain a binder suspension. After theophylline and ethyl cellulose were mixed in a high-speed agitating granulation machine, the resulting mixture was granulated while slowly dropping the above-described binder suspension thereto. A portion of the granules so obtained was dried at 80° C. for 4 hours, whereby a granular preparation was obtained. Preparations obtained by drying another portion of the granules at room temperature were provided as a control. A dissolution test was conducted using granules of 500 to 1,400 μm in particle size in each of the thus-obtained preparations. The results are presented in Table 2.

TABLE 2

| | | Dissolution rate (%) | | | | | | | | | | |
| --- | --- | --- | --- | --- | --- | --- | --- | --- | --- | --- | --- | --- |
| Elapsed time (min) | | 0 | 15 | 30 | 60 | 120 | 180 | 240 | 300 | 360 | 420 | 480 | 540 |
| Ex. 1 | Dried at room temperature (control) | 0.0 | 71.5 | 85.3 | 92.3 | 95.9 | 96.9 | 98.0 | 98.6 | 98.8 | 99.4 | 99.5 | 100.0 |
| | 80° C., 4 hr | 0.0 | 28.9 | 40.3 | 52.2 | 63.9 | 71.1 | 76.1 | 80.2 | 83.1 | 85.7 | 88.0 | 90.2 |
| Comp. Ex. 1 | Dried at room temperature (control) | 0.0 | 91.8 | 96.3 | 96.1 | 97.7 | 98.9 | 98.9 | 98.9 | 100.0 | 100.0 | 100.0 | 100.0 |
| | 80° C., 4 hr | 0.0 | 88.2 | 94.5 | 96.5 | 96.5 | 97.2 | 98.0 | 98.5 | 99.1 | 99.5 | 99.5 | 100.0 |

From Table 2, it has been confirmed that granules added with a plasticizer (Example 1) can be formed into a preparation having marked sustained release property when heated but that a preparation free of a plasticizer (Comparative Example 1) does not have any sustained release property.

EXAMPLES 2–3

In each example, granules were formed as in Example 1. Portions of the granules were dried at 40, 60 and 80° C. for 4 hours or 12 hours to obtain preparations, respectively. Further, a portion of the granules was dried at room temperature for a day to obtain a preparation as a control. Using granules of 500 to 1,400 μm in particle size in each of the thus-obtained preparations, a dissolution test was conducted as in Example 1. An investigation was carried out to check any influence by the drying temperature. The results are presented in Table 3.

TABLE 3

| Elapsed time (min) | | Dissolution rate (%) | | | | | | | | | | | |
|---|---|---|---|---|---|---|---|---|---|---|---|---|---|
| | | 0 | 15 | 30 | 60 | 120 | 180 | 240 | 300 | 360 | 420 | 480 | 540 |
| Control | Dried at room temperature | 0.0 | 71.5 | 85.3 | 92.3 | 95.9 | 96.9 | 98.0 | 98.6 | 98.8 | 99.4 | 99.5 | 100.0 |
| Ex. 2 | 40° C., 4 hr | 0.0 | 57.1 | 74.5 | 86.2 | 93.2 | 95.3 | 97.0 | 97.7 | 98.3 | 99.2 | 99.5 | 100.0 |
| | 60° C., 4 hr | 0.0 | 53.8 | 69.2 | 81.8 | 90.1 | 93.4 | 95.4 | 96.8 | 98.0 | 98.6 | 99.7 | 100.0 |
| | 80° C., 4 hr | 0.0 | 28.9 | 40.3 | 52.2 | 63.9 | 71.1 | 76.1 | 80.2 | 83.1 | 85.7 | 88.0 | 90.2 |
| Ex. 3 | 40° C., 12 hr | 0.0 | 76.0 | 86.6 | 92.4 | 95.9 | 97.1 | 97.7 | 98.3 | 98.8 | 99.5 | 99.5 | 100.0 |
| | 60° C., 12 hr | 0.0 | 53.8 | 69.3 | 81.3 | 90.1 | 93.3 | 95.3 | 96.8 | 98.0 | 98.6 | 99.7 | 100.0 |
| | 80° C., 12 hr | 0.0 | 35.4 | 47.5 | 60.7 | 74.2 | 82.2 | 87.4 | 91.2 | 94.1 | 96.2 | 98.2 | 100.0 |

From Table 3, it has been confirmed that a preparation having more prominent sustained-release property can be obtained as the drying temperature for granules becomes higher. On the other hand, it is also observed from the table that there is no difference in sustained release property between drying for 4 hours and drying for 12 hours.

EXAMPLE 4

Granules were formed as in Example 1. Portions of the granules were dried at 80° C. for 1, 2 or 3 hours to obtain preparations, respectively. Further, a portion of the granules was dried at room temperature to obtain a preparation as a control. Using granules of 500 to 1,400 μm in particle size in each of the thus-obtained preparations, a dissolution test was conducted as in Example 1. An investigation was carried out to check any influence by the drying temperature. The results are presented in Table 4.

From Table 4, it is observed that desired sustained-release property was substantially achieved by drying for 1 hour and that in drying for 1 to 4 hours, sustained release property slightly increased with the drying time.

EXAMPLE 5

In accordance with the formula shown in Table 5, granular preparations were produced as in Example 1. Using granules of 500 to 1,400 μm in particle size in the thus-obtained preparation, a dissolution test was conducted as in Example 1. An investigation was carried out to check any difference in the sustained release property of the preparations in which the plasticizer (TEC) had been increased relative to the polymer (EC). The results are presented in Table 6.

TABLE 5

| Formula (g) | Example 5 |
|---|---|
| Theophylline (THEO) | 15 |
| Ethyl cellulose (EC)*[1] | 100 |
| Triethyl citrate (TEC) | 35 |
| Polysolbate 80 (Tween 80) | Trace |
| Total | 150 |
| Tg (°C.) | 34*[2] |
| MFT (°C.) | 55*[2] |

*[1]Fine particle grade (volume mean particle size: 10.0 μm)

*[2]Estimated from the data shown in Chem. Pharm. Bull., 42(3), 656–662 (1994)

TABLE 4

| Elapsed time (min) | | Dissolution rate (%) | | | | | | | | | | | | |
|---|---|---|---|---|---|---|---|---|---|---|---|---|---|---|
| | | 0 | 15 | 30 | 60 | 120 | 180 | 240 | 300 | 360 | 420 | 480 | 540 | 600 |
| Control | Dried at room temperature | 0.0 | 84.4 | 90.5 | 93.1 | 94.9 | 95.1 | 95.6 | 96.0 | 96.6 | 97.1 | 96.6 | 97.1 | 97.1 |
| Ex. 4 | 80° C., 1 hr | 0.0 | 39.2 | 51.3 | 63.1 | 74.0 | 79.5 | 83.2 | 86.1 | 87.9 | 89.6 | 90.8 | 91.9 | 93.1 |
| | 80° C., 2 hr | 0.0 | 38.4 | 49.6 | 60.6 | 71.1 | 76.7 | 80.7 | 83.9 | 86.2 | 87.9 | 89.1 | 90.4 | 91.4 |
| | 80° C., 3 hr | 0.0 | 35.4 | 45.9 | 57.4 | 69.1 | 75.5 | 79.8 | 82.8 | 85.1 | 87.1 | 89.0 | 90.0 | 91.1 |

TABLE 6

| Elapsed time (min) | | 0 | 15 | 30 | 60 | 120 | 180 | 240 | 300 | 360 | 420 | 480 | 540 | 600 |
|---|---|---|---|---|---|---|---|---|---|---|---|---|---|---|
| Ex. 5 | Dried at room temperature (control) | 0.0 | 64.1 | 75.1 | 83.8 | 89.8 | 93.0 | 94.8 | 95.7 | 96.6 | 97.1 | 97.6 | 97.7 | 98.0 |
|  | 80° C., 4 hr | 0.0 | 21.6 | 27.7 | 33.6 | 40.2 | 45.4 | 49.2 | 52.8 | 55.4 | 57.8 | 60.1 | 61.9 | 63.8 |

From Table 6, it has been confirmed that sustained release property becomes more prominent by an increase in the amount of a plasticizer. This appears to be attributable to retarded release of the medicinal ingredient due to formation of the polymer into a homogeneous matrix under the influence of the plasticizer.

EXAMPLES 6–8

In each example, granular preparations were produced in accordance with the formula shown in Table 7 by following the procedures of Example 1. Using granules of 500 to 1,400 μm in particle size in the thus-obtained preparation, a dissolution test was conducted as in Example 1. An investigation was carried out to check any influence by the ratio of the polymer to the medicinal ingredient. The results are presented in Table 8.

TABLE 7

| Formula (g) | Ex. 6 | Ex. 7 | Ex. 8 |
|---|---|---|---|
| Theophylline (THEO) | 15 | 15 | 15 |
| Ethyl cellulose (EC)*[1] | 55 | 30 | 15 |
| Triethyl citrate (TEC) | 12.5 | 6.8 | 3.4 |
| Polysolbate 80 (Tween 80) | Trace | Trace | Trace |
| Total | 82.5 | 51.8 | 33.4 |
| Tg (°C.) | 36*[2] | 36*[2] | 36*[2] |
| MFT (°C.) | 65*[2] | 65*[2] | 65*[2] |

*[1]Fine particle grade (volume mean particle size: 10.0 μm)
*[2]Estimated from the data shown in Chem. Pharm. Bull., 42(3), 656–662 (1994)

From Table 8, it has been confirmed that sustained release property is exhibited more prominently as the ratio of the polymer (EC) to the medicinal ingredient (theophylline) increases. Examples 9–10 and Comparative Example 2

In each example, granular preparations were produced as in Example 1 except that the ingredients in the formula shown in Table 1 were mixed with the particle size of the polymer changed. Using granules of 500 to 1,400 μm in particle size in the thus-obtained preparation, a dissolution test was conducted as in Example 1. An investigation was carried out about any influence by the particle size of the polymer. The results are presented in Table 9.

TABLE 8

| Elapsed time (min) | | 0 | 15 | 30 | 60 | 120 | 180 | 240 | 300 | 360 | 420 | 480 | 540 | 600 |
|---|---|---|---|---|---|---|---|---|---|---|---|---|---|---|
| Ex. 6 | Dried at room temperature (control) | 0.0 | 78.6 | 87.9 | 92.3 | 94.6 | 96.2 | 96.8 | 97.3 | 97.8 | 98.7 | 98.7 | 98.9 | 99.0 |
|  | 80° C., 4 hr | 0.0 | 32.1 | 42.7 | 55.8 | 70.0 | 78.6 | 84.1 | 87.4 | 90.0 | 92.4 | 93.6 | 94.3 | 95.1 |
| Ex. 7 | Dried at room temperature (control) | 0.0 | 81.4 | 88.8 | 92.1 | 94.2 | 95.3 | 95.9 | 96.2 | 96.7 | 97.0 | 97.3 | 97.3 | 97.7 |
|  | 80° C., 4 hr | 0.0 | 43.6 | 58.7 | 74.4 | 86.9 | 91.8 | 94.0 | 95.5 | 96.3 | 96.8 | 97.3 | 97.8 | 98.0 |
| Ex. 8 | Dried at room temperature (control) | 0.0 | 82.8 | 91.7 | 94.8 | 96.0 | 96.4 | 96.5 | 96.7 | 97.0 | 97.2 | 97.3 | 97.6 | 97.7 |
|  | 80° C., 4 hr | 0.0 | 66.0 | 82.4 | 91.6 | 95.4 | 96.4 | 96.6 | 96.9 | 97.0 | 97.2 | 97.4 | 97.8 | 97.8 |

TABLE 9

| | Particle size (μm) | Elapsed time (min) | 0 | 15 | 30 | 60 | 120 | 180 | 240 | 300 | 360 | 420 | 480 | 540 |
|---|---|---|---|---|---|---|---|---|---|---|---|---|---|---|
| Ex. 9 | 10.0 | Dried at room temperature (control) | 0.0 | 71.5 | 85.3 | 92.3 | 95.9 | 96.9 | 98.0 | 98.6 | 98.8 | 99.4 | 99.5 | 100.0 |
| | | 80° C., 4 hr | 0.0 | 28.9 | 40.3 | 52.2 | 63.9 | 71.1 | 76.1 | 80.2 | 83.1 | 85.7 | 88.0 | 90.2 |
| Ex. 10 | 22.0 | Dried at room temperature (control) | 0.0 | 83.4 | 91.6 | 95.8 | 97.4 | 98.1 | 98.2 | 98.5 | 98.9 | 99.3 | 99.5 | 99.9 |
| | | 80° C., 4 hr | 0.0 | 49.8 | 63.9 | 76.0 | 86.3 | 91.0 | 94.0 | 95.9 | 97.1 | 98.2 | 98.9 | 99.6 |
| Comp. Ex. 2 | 59.7 | Dried at room temperature (control) | 0.0 | 80.7 | 87.9 | 92.8 | 94.9 | 97.1 | 97.6 | 98.4 | 98.9 | 99.0 | 99.5 | 99.7 |
| | | 80° C., 4 hr | 0.0 | 69.8 | 83.3 | 91.3 | 95.6 | 97.4 | 98.0 | 98.4 | 98.9 | 99.5 | 99.8 | 100.0 |

From Table 9, it is observed that the sustained release property of a granular preparation becomes more prominent as the average particle size of the added polymer becomes smaller and that the addition of the polymer of 59.7 μm in average particle size failed to provide any granular preparation having sustained release property.

EXAMPLE 11–12

In each example, granular preparations of the formulation shown in Table 10 were produced in a manner similar to Example 1. Using granules of 500 to 1,400 μm in particle size in the thus-obtained preparation, a dissolution test was conducted as in Example 1. An investigation was carried out to check its sustained release property. The results are presented in Table 11.

TABLE 10

| Formula (g) | Example 11 | Example 12 |
|---|---|---|
| Theophylline (THEO) | 15 | 15 |
| Ethyl cellulose (EC)[*1] | 110 | — |
| Hydroxypropylmethyl-cellulose acetate succinate (HPMCAS)[*2] | — | 110 |
| Triethyl citrate (TEC) | — | 25 |
| Triacetone | 25 | — |
| Polysorbate 80 (Tween 80) | Trace | Trace |
| Total | 150 | 150 |
| Tg (°C.) | — | — |
| MFT (°C.) | 35–40[*3] | 15–20[*3] |

[*1]Fine particle grade (volume mean particle size: 10.0 μm)
[*2]Fine particle grade (volume mean particle size: 8.1 μm); AS-HF, Shin-Etsu Chemical Co., Ltd.
[*3]Portions of a suspension of the polymer in an aqueous solution of the plasticizer were added to Petri dishes and stored at different temperatures, respectively. About 48 hours later, the Petri dishes were taken out and observed to determine whether or not a film had been formed. An MFT was considered to exist between a lowest temperature at which a transparent film was formed and a highest temperature at which a transparent film was not formed.

TABLE 11

| | Elapsed time (min) | 0 | 15 | 30 | 60 | 120 | 180 | 240 | 300 | 360 | 420 | 480 | 540 | 600 |
|---|---|---|---|---|---|---|---|---|---|---|---|---|---|---|
| Ex. 11 | Dried at room temperature (control) | 0.0 | 90.9 | 95.7 | 97.8 | 98.6 | 99.3 | 99.6 | 99.7 | 99.8 | 99.8 | 100.0 | 100.0 | 100.0 |
| | 80° C., 4 hr | 0.0 | 69.2 | 76.1 | 80.6 | 84.4 | 87.3 | 89.1 | 90.5 | 91.4 | 92.3 | 93.3 | 93.9 | 94.4 |
| Ex. 12 | Dried at room temperature (control) | 0.0 | 15.5 | 20.7 | 28.3 | 38.1 | 45.4 | 51.5 | 56.3 | 60.3 | 64.2 | 67.2 | 69.9 | 72.4 |
| | 80° C., 4 hr | 0.0 | 15.9 | 20.2 | 26.7 | 36.9 | 44.9 | 51.5 | 56.8 | 61.0 | 64.9 | 67.8 | 70.9 | 73.2 |

From Table 11, it has been confirmed that the use of triacetin as a plasticizer for ethylcellulose (Example 11) and the use of HPMCAS as a polymer (Example 12) both provided preparations having sustained release property, respectively.

EXAMPLE 13

Preparations of the formula shown in Table 1 were produced by a granulation method different from that employed in Example 1, and its sustained release property was investigated. First, polysorbate 80 was dissolved in 75 ml of water, in which triethyl citrate was homogeneously suspended to obtain a suspension. After theophylline and ethyl cellulose were mixed in a high-speed agitating granulation machine, the resulting mixture was kneaded while slowly dropping the above-described suspension thereto. A portion of the mass so kneaded was granulated through an extruding granulation machine (which was equipped with a screen of 0.5 mm-in opening) and then processed in a "Marumerizer" (trade mark; manufactured by Fuji Pandal Co., Ltd.), whereby granules were obtained. A portion of the granules were dried at 80° C. for 4 hours so that a granular preparation was obtained. Another portion of the granules was dried at room temperature to provide a control. A dissolution test was conducted using granules of 355 to 500 μm in particle size in each of the thus-obtained preparations. The results are presented in Table 12.

machine, the resulting mixture was kneaded while slowly dropping the above-described suspension thereto. Next, the mass so kneaded and 10 ml of water were placed in a kneader and kneaded there. The thus-obtained kneaded mass was granulated through an extruding granulation machine (which was equipped with a screen of 0.5 mm in opening) and then processed in a "Marumerizer" (trade mark; manufactured by Fuji Pandal Co., Ltd.), whereby granules were obtained. A portion of the granules were dried at 80° C. for 4 hours so that a granular preparation was obtained. Another portion of the granules was dried at room temperature to provide a control. A dissolution test similar to that conducted in Example 1 was conducted on the granules of the entire particle size range in the preparation so obtained. The results are presented in Tables 13 and 14.

TABLE 13

| Particle size | (%) |
| --- | --- |
| 850 μm and greater | 6.2 |
| 850–500 μm | 73.7 |
| 500–355 μm | 14.3 |
| 355–250 μm | 4.6 |
| 250 μm and smaller | 1.2 |
|  | 100.0 |

TABLE 12

| | | Dissolution rate (%) | | | | | | | | | | | |
| --- | --- | --- | --- | --- | --- | --- | --- | --- | --- | --- | --- | --- | --- |
| Elapsed time (min) | | 0 | 15 | 30 | 60 | 120 | 180 | 240 | 300 | 360 | 420 | 480 | 540 | 600 |
| Ex. 13 | Dried at room temperature (control) | 0.0 | 94.3 | 97.4 | 98.2 | 98.4 | 98.8 | 99.0 | 99.2 | 99.5 | 99.6 | 99.8 | 100.0 | 100.0 |
| | 80° C., 4 hr | 0.0 | 33.6 | 43.0 | 54.8 | 68.6 | 76.5 | 81.7 | 85.5 | 88.1 | 90.3 | 92.1 | 93.3 | 94.6 |

From Table 12, it is observed that a preparation having sustained release property can be obtained even when granulation is conducted in a manner different from that employed in Example 1 and the resultant granules are heat-treated as in Example 1.

TABLE 14

| | | Dissolution rate (%) | | | | | | | | | | | |
| --- | --- | --- | --- | --- | --- | --- | --- | --- | --- | --- | --- | --- | --- |
| Elapsed time (min) | | 0 | 15 | 30 | 60 | 120 | 180 | 240 | 300 | 360 | 420 | 480 | 540 | 600 |
| Ex. 14 | Dried at room temperature (control) | 0.0 | 56.5 | 67.4 | 77.3 | 85.2 | 88.4 | 90.7 | 92.2 | 93.3 | 94.1 | 94.7 | 95.4 | 96.0 |
| | 80° C., 4 hr | 0.0 | 46.2 | 55.3 | 66.0 | 77.3 | 83.8 | 87.7 | 90.4 | 92.4 | 93.7 | 94.8 | 95.6 | 96.3 |

EXAMPLE 14

Preparations of the formula shown in Example 12 (Table 10) were produced by a granulation method different from that employed in Example 12, and its sustained release property was investigated. First, polysorbate 80 was dissolved in 50 ml of water, in which triethyl citrate was homogeneously suspended to obtain a suspension. After theophylline and hydroxypropyl methylcellulose acetate succinate were mixed in a high-speed agitating granulation Like the granules produced by the agitating granulation method in Example 12, similar sustained release property was observed on both granules of a preparation dried under heat and those of a preparation dried at room temperature. The dissolution test in this Example showed somewhat faster dissolution property than that in Example 12 probably because the dissolution test in this Example was conducted using the granules of the entire particle size range obtained.

EXAMPLE 15

Following the formula shown in Table 1, preparations were produced by slightly changing the production process of Example 13. The sustained release property of the preparation was investigated. Further, polysorbate 80 was dissolved in 50 ml of water, in which triethyl citrate was homogeneously suspended to obtain a suspension. After theophylline and ethylcellulose were mixed in a high-speed agitating granulation machine, the resulting mixture was kneaded while slowly dropping the above-described suspension thereto. Next, the mass so kneaded and 30 ml of water were placed in a kneader and kneaded there. The thus-obtained kneaded mass was granulated through an extruding granulation machine (which was equipped with a screen of 0.8 mm in opening) and then processed in a "Marumerizer" (trade mark; manufactured by Fuji Pandal Co., Ltd.), whereby granules were obtained. A portion of the granules were dried at 80° C. for 4 hours so that a granular preparation was obtained. Another portion of the granules was dried at room temperature to provide a control. A dissolution test similar to that conducted in Example 1 was conducted on granules of 500 to 850 μm in particle size in each of the preparations so obtained. The results are presented in Table 15.

polysorbate 80 was dissolved in 50 ml of water, in which triethyl citrate was homogeneously suspended to obtain a suspension. Further, hydroxypropyl cellulose was dissolved in 30 ml of water and the solution so prepared was mixed with the suspension. After theophylline and ethylcellulose were mixed in a high-speed agitating granulation machine, the resulting mixture was kneaded while slowly dropping the above-described suspension thereto. Next, the mass so kneaded was placed in a kneader and kneaded there. The thus-obtained kneaded mass was granulated through an extruding granulation machine (which was equipped with a screen of 0.5 mm in opening) and then processed in a "Marumerizer" (trade mark; manufactured by Fuji Pandal Co., Ltd.), whereby granules were obtained. A portion of the granules were dried at 80° C. for 4 hours so that a granular preparation was obtained. Another portion of the granules was dried at room temperature to provide a control. A dissolution test similar to that conducted in Example 1 was conducted on granules of 355 to 500 μm in particle size in each of the preparations so obtained. The results are presented in Table 17.

TABLE 15

| | | Dissolution rate (%) | | | | | | | | | | | |
|---|---|---|---|---|---|---|---|---|---|---|---|---|---|
| Elapsed time (min) | | 0 | 15 | 30 | 60 | 120 | 180 | 240 | 300 | 360 | 420 | 480 | 540 | 600 |
| Ex. 15 | Dried at room temperature (control) | 0.0 | 95.4 | 96.5 | 96.7 | 97.0 | 97.4 | 97.6 | 97.7 | 98.0 | 98.0 | 98.3 | 98.4 | 98.6 |
| | 80° C., 4 hr | 0.0 | 24.3 | 31.2 | 41.4 | 55.3 | 64.3 | 70.8 | 76.1 | 80.2 | 83.6 | 86.7 | 89.1 | 91.2 |

As the granules obtained by conducting the extrusion granulation through the 0.8 mm screen were greater in particle size than those obtained through the 0.5 mm screen in Example 13, marked sustained-release property was exhibited.

EXAMPLES 16 AND 17

In each example, granular preparations of the formula shown in Table 16 were produced as will be described below and its sustained release property was investigated. First,

TABLE 16

| Formula (g) | Example 16 | Example 17 |
|---|---|---|
| Theophylline (THEO) | 15 | 15 |
| Ethyl cellulose (EC) | 110 | 110 |
| Triethyl citrate (TEC) | 25 | 25 |
| Hydroxypropyl cellulose (HPC-L) | 3 | 8 |
| Polysorbate 80 (Tween 80) | Trace | Trace |
| Total | 153 | 158 |

TABLE 17

| | | Dissolution rate (%) | | | | | | | | | | | |
|---|---|---|---|---|---|---|---|---|---|---|---|---|---|
| Elapsed time (min) | | 0 | 15 | 30 | 60 | 120 | 180 | 240 | 300 | 360 | 420 | 480 | 540 | 600 |
| Ex. 16 | Dried at room temperature (control) | 0.0 | 92.5 | 95.9 | 96.4 | 96.7 | 97.0 | 97.0 | 97.3 | 97.6 | 97.8 | 97.7 | 98.1 | 98.3 |
| | 80° C., 4 hr | 0.0 | 32.7 | 45.1 | 71.7 | 82.8 | 88.7 | 91.8 | 93.3 | 94.5 | 95.1 | 95.6 | 96.0 | 96.3 |
| Ex. 17 | Dried at room temperature (control) | 0.0 | 95.0 | 96.0 | 96.4 | 96.6 | 96.8 | 97.2 | 97.3 | 97.7 | 97.9 | 98.0 | 98.2 | 98.3 |
| | 80° C., 4 hr | 0.0 | 55.3 | 73.6 | 85.7 | 92.3 | 94.7 | 95.7 | 96.3 | 96.9 | 97.2 | 97.5 | 97.7 | 98.1 |

It has been confirmed that addition of hydroxypropyl cellulose, a water-soluble substance, into granules makes it possible to control the release rate.

EXAMPLE 18

Following the formula shown in Table 18, granular preparations were produced as will be described below, and its sustained release property was investigated. First, triethyl citrate was dissolved in 60 ml of water to obtain a suspension. After theophylline and ethylcellulose were mixed in a high-speed agitating granulation machine, the resulting mixture was kneaded while slowly dropping the above-described suspension thereto. Next, the mass so kneaded and 40 ml of water were placed in a kneader and kneaded there. The thus-obtained kneaded mass was granulated through an extruding granulation machine (which was equipped with a screen of 0.5 mm in opening) and then processed in a "Marumerizer" (trade mark; manufactured by Fuji Pandal Co., Ltd.), whereby granules were obtained. A portion of the granules were dried at 80° C. for 4 hours so that a granular preparation was obtained. Another portion of the granules was dried at room temperature to provide a control. A dissolution test similar to that conducted in Example 1 was conducted on granules of 355 to 500 $\mu$m in particle size in each of the preparations so obtained. The results are presented in Table 19.

TABLE 18

| Formula (g) | Example 18 |
|---|---|
| Theophylline (THEO) | 15 |
| Ethyl cellulose (EC) | 110 |
| Triethyl citrate (TEC) | 25 |
| Total | 150 |

CAPABILITY OF EXPLOITATION IN INDUSTRY

According to the present invention, granular preparations having excellent sustained release property and high safety to the human body can be easily obtained in a simple manner.

We claim:

1. Sustained-release granular preparations obtained by wet-granulating an aqueous suspension, which comprises a medicinal ingredient, fine particulate hydroxypropyl methylcellulose acetate succinate having an average particle size not greater than 50 $\mu$m and a plasticizer, into granules and treating said granules at a temperature not less than the lower one of a minimum film-forming temperature and glass transition temperature of a mixture of said polymer and said plasticizer.

2. Sustained-release granular preparations according to claim 1, wherein said average particle size of said fine particulate polymer is from 1 $\mu$m to 20 $\mu$m.

3. Sustained-release granular preparations according to claim 1, wherein said plasticizer is an alkyl citrate.

4. Sustained-release granular preparations according to claim 1, wherein said plasticizer is a polyethylene glycol.

5. Sustained-release granular preparations according to claim 1, wherein said plasticizer is propylene glycol.

6. Sustained-release granular preparations according to claim 1, wherein said plasticizer is a glycerin mono-, di- or tri-fatty acid ester.

7. Sustained-release granular preparations according to claim 1, wherein said plasticizer is an alkyl phthalate.

8. Sustained-release granular preparations according to claim 1, obtained by treating said granules at a temperature

TABLE 19

| | | Dissolution rate (%) | | | | | | | | | | | | |
|---|---|---|---|---|---|---|---|---|---|---|---|---|---|---|
| Elapsed time (min) | | 0 | 15 | 30 | 60 | 120 | 180 | 240 | 300 | 360 | 420 | 480 | 540 | 600 |
| Ex. 18 | Dried at room temperature (control) | 0.0 | 90.1 | 94.1 | 95.4 | 96.2 | 96.5 | 96.6 | 97.0 | 97.0 | 97.4 | 97.4 | 97.5 | 97.9 |
| | 80° C., 4 hr | 0.0 | 45.8 | 50.9 | 56.0 | 62.2 | 66.3 | 69.6 | 72.8 | 75.5 | 77.9 | 79.9 | 82.2 | 84.1 |

Sustained release property similar to that shown in Example 13 was also exhibited without addition of polysorbate 80.

not less than said glass transition temperature.

* * * * *